United States Patent [19]

Kamuro et al.

[11] Patent Number: 4,751,226
[45] Date of Patent: Jun. 14, 1988

[54] PYRAZOLOISOQUINOLINE DERIVATIVES, PLANT GROWTH REGULATING COMPOSITIONS, AND METHOD OF USE THEREFOR

[75] Inventors: Yasuo Kamuro, Ibaraki; Eiji Taniguchi; Katsuji Watanabe, both of Fukuoka, all of Japan

[73] Assignee: Fujisawa Pharmaceutical Co., Ltd., Osaka, Japan

[21] Appl. No.: 901,371

[22] Filed: Aug. 28, 1986

[30] Foreign Application Priority Data

Sep. 12, 1985 [JP] Japan .................................. 60-202856

[51] Int. Cl.[4] ..................... A01N 43/48; C07D 471/04
[52] U.S. Cl. ............................................ 71/92; 546/84
[58] Field of Search .................. 546/84; 514/294, 292; 71/92, 76

[56] References Cited

U.S. PATENT DOCUMENTS 4,612,318  9/1986  Winters ............................... 514/293

OTHER PUBLICATIONS

Potts, *Comprehensive Heterocyclic Chemistry*, vol. 5, Part 4A, 1984 p. 121.
*Plant Physiology* (1976) 57, pp. 839–841, Beyer et al., A New Class of Synthetic Auxin Transport Inhibitors.

*Primary Examiner*—Richard A. Schwartz
*Assistant Examiner*—Zinna Northington
*Attorney, Agent, or Firm*—Oblon, Fisher, Spivak, McClelland & Maier

[57] ABSTRACT

The invention relates to plant growth regulating compounds which are pyrazoloisoquinoline derivatives.

18 Claims, No Drawings

PYRAZOLOISOQUINOLINE DERIVATIVES, PLANT GROWTH REGULATING COMPOSITIONS, AND METHOD OF USE THEREFOR

This invention relates to novel compounds useful as agrochemicals. More particularly, it relates to novel pyrazoloisoquinoline derivatives which have plant growth regulating activities, to a process for preparation thereof and to a plant growth regulating composition comprising the same.

So far, several substances capable of inhibiting the transport of the plant hormone auxin in the plant body (auxin transport inhibitors) have been known to be useful as plant growth regulators. As a typical example, there may be mentioned 2,3,5-triiodobenzoic acid (TIBA). This, however, is not always satisfactory as a plant growth regulator. Appearance of substances superior in activity to TIBA is desired.

In view of the above, the present inventors conducted intensive investigations and, as a result, found that pyrazoloisoquinoline derivatives of the general formula (I) as mentioned below have potent auxin transport inhibiting activity. Continued investigations based on this finding have now led to completion of this invention.

Pyrazoloisoquinoline derivatives of this invention can be represented by the following general formula (I):

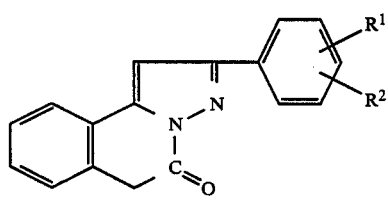

wherein $R^1$ and $R^2$ are the same or different and each is a hydrogen or halogen atom or a nitro, lower alkyl, halogen-substituted (lower) alkyl, lower alkoxy, lower alkylthio or aryloxy group.

The objective compounds (I) of this invention are novel compounds and can be prepared by the process illustrated below.

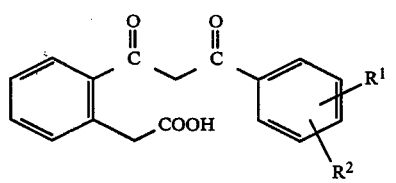

or salt thereof or reactive derivative thereof at the carboxyl group

↓ Hydrazine or salt thereof

-continued

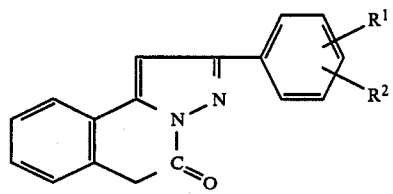

In the above formulas, $R^1$ and $R^2$ are as defined above.

The definitions of symbols used in the above general formulas are described below. Unless otherwise specified, the term "lower" is used to indicate that the relevant group contains 1 to 6 carbon atoms.

"Lower alkyl group" means a straight or branched, saturated lower aliphatic hydrocarbon residue. Preferred examples thereof may include methyl, ethyl, propyl, isopropyl, butyl, isobutyl, tert-butyl, pentyl, hexyl and the like.

As the "halogen-substituted (lower) alkyl group", there may be exemplified those groups which are derived from the groups given above as examples of the "lower alkyl group" by substitution with one or more fluorine, chlorine, bromine and/or iodine atoms optionally on one or more carbon atoms thereof. A most preferred example of such group is trifluoromethyl, for instance.

The term "lower alkoxy group" means a group consisting of a straight or branched, saturated lower aliphatic hydrocarbon residue and an oxygen atom bonded to said residue. Preferred examples thereof may include methoxy, ethoxy, propoxy, isopropoxy, butoxy, isobutoxy, tert-butoxy, pentyloxy, hexyloxy and the like.

The term "lower alkylthio" means a group consisting of a straight or branched, saturated aliphatic hydrocarbon residue and a sulfur atom bonded to said residue. Preferred examples of such group may include methylthio, ethylthio, propylthio, isopropylthio, butylthio and the like.

The term "aryloxy group" means a group consisting of a monocyclic or bicyclic aromatic hydrocarbon residue and an oxygen atom bonded to said residue. Preferred examples of such group may include phenoxy, tolyloxy, xylyloxy, mesityloxy, or naphthoxy.

The term "halogen" includes fluorine, chlorine, bromine and iodine.

The objective compounds (I) of this invention can be prepared by reacting the compound (II), a salt thereof or a reactive derivative thereof at the carboxyl group with hydrazine or a salt thereof.

The compound (II) to be used here as a starting material is either a known compound (for the compound in which $R^1$ and $R^2$ are each hydrogen, refer to Abstracts of Papers for the 1984 Meeting of the Japan Society for Chemical Regulation of Plants, pages 20–21 and Abstracts of Papers for the 1985 Meeting of the Pesticide Science Society of Japan, page 36) or a novel compound. Such novel compound can be prepared by the same method as described in the references cited above.

The salt of compound (II) includes, among others, salts with inorganic bases, for example alkali metal salts such as sodium salt and potassium salt, alkaline earth metal salts such as magnesium salt and calcium salt, and ammonium salt, and salts with organic bases such as trimethylamine salt and triethylamine salt.

The reactive derivative of compound (II) at the carboxyl group thereof may include, among others, acid anhydrides, esters, acid halides, acid azide and other reactive forms in conventional use.

The salt of hydrazine includes salts with inorganic acids, such as hydrochloric acid, hydrobromic acid, sulfuric acid and phosphoric acid, and salts with organic acids, such as acetic acid, trifluoroacetic acid and propionic acid.

This reaction is carried out in a solvent which does not affect the reaction adversely, for example an alcohol, such as methanol or ethanol, dimethylformamide or tetrahydrofuran. When hydrazine hydrate is used, for instance, good results can often be obtained by carrying out the reaction with heating under reflux.

The objective compounds (I) are isolated in the conventional manner by extraction, recrystallization and/or chromatography, for instance.

The objective compounds (I) of this invention have potent auxin transport inhibiting activity and are useful as plant growth regulators. For example, they can be used as plant growth regulators for the purpose of controlling the plant height of vegetables such as tomato, eggplant and green pepper, controlling the height of flowering plants such as chrysanthemum, carnation and cosmos, controlling the plant height of grasses (monocotyledon) such as paddy-rice plant, wheat, barley and the like, inhibiting turion development in fruit trees such as apple trees and pear trees, controlling the abscission formation of flowers, fruits or leaves of the plants mentioned above, promoting tillering or branching of the plants mentioned above, increasing in yield of cereal crops such as grasses (e.g. paddy-rice plant, wheat, barley, etc.) and the like, increasing in yield of leguminous crops such as soybean, azuki-bean, peanut, pease and the like, or ncreasing in yield of potato.

The mode of application of the plant growth regulators of this invention may vary depending on the plant species to be treated. Generally, however, the plant growth regulators are suitably applied in the manner of foliage application by spraying. The concentration for application may vary depending on the plant to be treated but generally is within the range of about 1–5,000 ppm.

For use as plant growth regulators in accordance with this invention, the compounds (I) are used, depending on the situation in which they are to be applied, in the form of powders, granules, tablets, wettable powders, emulsions, etc. as prepared by mixing them with a variety of carriers to be used in agrochemical preparations. The carriers may be solids or liquids or combinations thereof. For example, talc, clay, kaolin, diatomaceous earth, calcium carbonate, potassium chlorate, potassium nitrate, nitrocellulose, starch, gum arabic, water, alcohol, benzene, acetone and so forth are used as the carriers. Furthermore, auxiliaries commonly used in agrochemical preparations, such as spreaders and emulsifiers, may be added as necessary.

The preparations thus obtained may be used either alone as they are or in admixture with fungicides, insecticides, herbicides, other plant growth regulators and/or fertilizers.

In the following, the effects of the plant growth regulators of this invention are illustrated by giving several test examples.

TEST EXAMPLE 1

(Test for root growth inhibiting activity against paddy rice plant at germination stage)

A filter paper piece was placed in a dish, 9 cm in diameter, to cover the bottom of the dish. An acetone solution of the test compound was dropped onto the filter paper piece in an amount sufficient to give a concentration specified below. After evaporation of the acetone, 10 ml of water was poured into the dish and then 7 paddy rice seed grains (Koshihikari cultivar) at the stage of forced sprouting were placed in the dish. After 7 days of continuous exposure to fluorescent lamp light at a constant temperature of 25° C., the extent of root growth was evaluated by scoring according to the following criteria:

Score 3:75% or more inhibition as compared with the untreated group

Score 2:50–74% inhibition as compared with the untreated group

Score 1:25–49% inhibition as compared with the untreated group

Score 0:Less than 24% inhibition as compared with the untreated group

The results thus obtained are shown in the table which follows.

| Compound (in terms of Example No. given later) | Extent of root growth | | |
|---|---|---|---|
| | 100 ppm | 20 ppm | 4 ppm |
| 1 | 2 | 2 | 1 |
| 2 | 2 | 2 | 1 |
| 3 | 2 | 2 | 2 |
| 4 | 2 | 2 | 1 |
| 5 | 3 | 3 | 1 |
| 6 | 2 | 2 | 1 |
| 7 | 3 | 2 | 1 |
| 8 | 3 | 2 | 1 |
| 9 | 2 | 2 | 1 |
| 10 | 2 | 2 | 1 |
| 11 | 1 | 1 | 0 |
| 12 | 2 | 2 | 1 |
| 14 | 2 | 2 | 0 |
| 15 | 2 | 2 | 2 |
| 16 | 2 | 2 | 1 |
| 17 | 3 | 2 | 2 |
| 18 | 3 | 1 | 0 |
| 19 | 2 | 2 | 2 |
| 20 | 2 | 1 | 1 |
| 21 | 2 | 1 | 0 |
| 22 | 2 | 2 | 2 |
| 23 | 2 | 2 | 2 |
| 24 | 2 | 2 | 1 |
| 25 | 2 | 2 | 2 |
| 26 | 2 | 2 | 2 |
| Control (2,3,5-triiodobenzoic acid) | 2 | 1 | 1 |

TEST EXAMPLE 2

(Grass height controlling and tiller increasing activity test of paddy rice plant):

The seed of paddy rice (cultivar: Koshihikari) was sown, one seed grain per 4×4 cm pot and the test emulsion was sprayed at the four-leaf stage. The test emulsion was prepared by diluting an emulsifiable concentrate containing one of the under-mentioned compounds as prepared in the routine manner with sufficient water to make one of the under-mentioned concentrations. The test was performed in 4 pots per group.

Two weeks after application of the test emulsion, the average grass height and the total number of tillers for 4 pots per group were investigated.

The results are shown in the following table. The grass heights are in percent extensions relative to the untreated group.

| Compound (in terms of Example No. given later) | Grass height | | | Number of tillers | | |
|---|---|---|---|---|---|---|
| | 30 ppm | 10 ppm | 3 ppm | 30 ppm | 10 ppm | 3 ppm |
| 1 | 85 | 96 | 90 | 8 | 8 | 8 |
| 2 | 60 | 62 | 63 | 10 | 13 | 11 |
| 3 | 54 | 63 | 65 | 12 | 11 | 9 |
| 5 | 75 | 85 | 90 | 9 | 9 | 8 |
| 6 | 48 | 60 | 64 | 11 | 13 | 12 |
| 7 | 79 | 75 | 98 | 11 | 8 | 8 |
| 8 | 69 | 75 | 89 | 9 | 7 | 8 |
| 9 | 79 | 87 | 92 | 11 | 9 | 8 |
| 10 | 81 | 81 | 90 | 9 | 8 | 8 |
| 11 | 90 | 98 | 93 | 8 | 6 | 6 |
| 12 | 65 | 73 | 88 | 10 | 12 | 8 |
| Control (2,3,5-triiodobenzoic acid) | 90 | 96 | 92 | 7 | 8 | 7 |
| No spraying | 52 cm (100%) | | | 7/4 pots | | |

TEST EXAMPLE 3

(Grass height controlling and tiller increasing activity test of paddy rice plant):

The test was conducted by the same method as that of Text Example 2 except that the compound of Example 4 was employed as the test compound.

The results are shown in the following table.

| Compound (in terms of Example No. given later) | Grass height | | | Number of tillers | | |
|---|---|---|---|---|---|---|
| | 30 ppm | 10 ppm | 3 ppm | 30 ppm | 10 ppm | 3 ppm |
| 4 | 66 | 70 | 76 | 16 | 16 | 13 |
| No spraying | 52 cm (100%) | | | 4/4 pots | | |

TEST EXAMPLE 4

(Auxin transport inhibiting activity test):

A 13-mm segment of the kidney bean stalk after 13 days of growing under exposure to artificial light was excised. The segment was fitted, at the apical end thereof, with an agar block containing 1 ppm of IAA-2-$^{14}$C (30 mCi/mmol). The whole was allowed to stand in a humid environment under artificial lighting for 4 hours and the IAA transported from the top end agar block to the basal end plain agar block was assayed using a liquid scintillation counter.

Twenty agar blocks per compound were used and the results were expressed as the mean of triplicates per concentration. The percent transported values were calculated in terms of activity ratio relative to the untreated group.

The results obtained are shown in the following table.

| Compound (in terms of Example No. given later) | Concentration (M) | | | |
|---|---|---|---|---|
| | $10^{-6}$ | $10^{-7}$ | $10^{-8}$ | $10^{-9}$ |
| 1 | 15(%) | 56 | 105 | |
| 10 | 23 | 20 | 68 | 105 |
| Control | | 64 | 86 | |

| Compound (in terms of Example No. given later) | Concentration (M) | | | |
|---|---|---|---|---|
| | $10^{-6}$ | $10^{-7}$ | $10^{-8}$ | $10^{-9}$ |
| (2,3,5-triiodobenzoic acid) | | | | |

TEST EXAMPLE 5

(Test for yield increasing of wheat):

The seeds of wheat (cultivar: Nohrin-61-GO) were sown into the field at autumn and grown under the ordinary cultivation practices.

The test emulsion was prepared according to the method of Example 30 given later with sufficient water to make one of the under-mentioned concentrations. The spray timing was at the beginning of tillering stage, and at 10 days before maximum tiller number stage. Water volume for spraying was 100 ml per m$^2$. The yield (panicle weight) were investigated.

The results are shown in the following table. The yield are in percent relative to the untreated group.

| Treatment timing | Yield (total panicle weight/5 m$^2$) Test compound (the compound of Example 4 given later) | | | |
|---|---|---|---|---|
| | 50 ppm | 16.7 ppm | 5.6 ppm | 0 (untreated) |
| at the beginning of tillering stage | 117% | 115 | 135 | 100 (520 g/5 m$^2$) |
| at 10 days before maximum tiller number | 138 | 130 | 142 | |

TEST EXAMPLE 6

(Test for yield increasing of potato):

Potato (cultivar: Mayqueen) were grown under the ordinary cultivation method.

The test emulsion was prepared according to the method of Example 30 given later with sufficient water to make one of the under-mentioned concentrations.

The spray timing was one month before harvest. Water volume for spraying was 100 ml per m$^2$.

The average yield (total tuber weight) were investigated.

The results are shown in the following table. The yield are in percent relative to the untreated group.

| | Test compound (the compound of Example 4 given later) | | |
|---|---|---|---|
| | 50 ppm | 6 ppm | 0 (untreated) |
| Yield (total tuber weight/10 m$^2$) | 112.6% | 95.6 | 100 (25.9 kg/10 m$^2$) |

TEST EXAMPLE 7

(Test for young fruits thinning of apple):

15 years old trees (cultivar: Jonasan) were treated.

The test emulsion was prepared according to the method of Example 30 given later with sufficient water to make one of the under-mentioned concentrations.

The spray timing was at two weeks after full-blossom.

Water volume for spray was 500 l per 10a.

20 Days after treatment, the average fruit drop ratio were investigated. The fruit drop ratio is in percent relative to number of fruits at the time of spraying the test emulsion.

The results are shown in the following table.

| Test compound (The compound of Example 4 given later) | Fruit-drop ratio (%) | |
|---|---|---|
| | Central fruit | Lateral fruit |
| 50 ppm | 74.3 | 88.8 |
| 16.7 ppm | 66.2 | 78.9 |
| 5.6 ppm | 73.0 | 86.4 |
| 0 (untreated) | 53.8 | 68.9 |

The following Examples are given for the purpose of illustrating this invention.

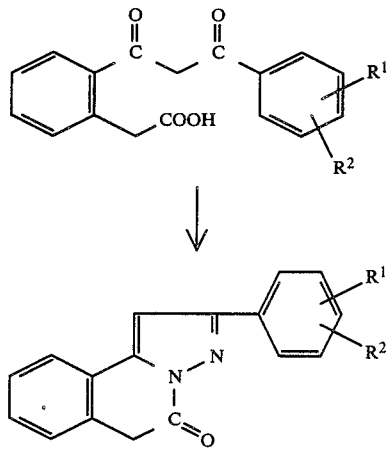

EXAMPLE 1

Production of compound wherein, in above formulas, $R^1$ and $R^2$ are each hydrogen):

To ethanol (10 ml), there were added 2-(1,3-dioxo-3-phenylpropyl) phenylacetic acid (1.42 g) and hydrazine hydrate (0.25 g), followed by heating under reflux for 2 hours. Thereafter, the reaction mixture was cooled to give 2-phenyl-5,6-dihydropyrazolo-[5,1-a]isoquinolin-5-one (1.06 g). Mp. 181°–183° C.

In substantially the same manner as in Example 1, the following compounds were obtained:

| Example No. | $R^1$ | $R^2$ | mp (°C.) |
|---|---|---|---|
| 2 | 4-Bromo | Hydrogen | 222–224 |
| 3 | 4-Methoxy | Hydrogen | 195–197 |
| 4 | 4-Fluoro | Hydrogen | 192–194 |
| 5 | 3-Chloro | Hydrogen | 218–220 |
| 6 | 4-Trifluoromethyl | Hydrogen | 213–216 |
| 7 | 3-Bromo | Hydrogen | 217–219 |
| 8 | 4-Methyl | Hydrogen | 190–192 |
| 9 | 3-Methyl | Hydrogen | 199–200 |
| 10 | 3-Fluoro | Hydrogen | 178–179 |
| 11 | 4-Methylthio | Hydrogen | 183–184 |
| 12 | 3-Chloro | 4-Chloro | 248–250 |
| 14 | 4-Nitro | Hydrogen | 252–254 |
| 15 | 4-Chloro | Hydrogen | 228–230 |
| 16 | 2-Methyl | Hydrogen | 141–143 |
| 17 | 2-Chloro | Hydrogen | 186–188 |
| 18 | 3-Methoxy | 4-Methoxy | 186–188 |
| 19 | 4-Isopropyl | Hydrogen | 169–172 |
| 20 | 2-Chloro | 4-Chloro | 248–250 |
| 21 | 3-Phenoxy | Hydrogen | 155–157 |
| 22 | 3-Methoxy | Hydrogen | 195–197 |
| 23 | 4-Ethyl | Hydrogen | 170–171 |
| 24 | 3-Nitro | Hydrogen | 262–269 |
| 25 | 2-Methoxy | Hydrogen | 217–220 |
| 26 | 3-Trifluoromethyl | Hydrogen | 223–224 |

EXAMPLE 27

(Plant growth regulating composition):

| 2-Phenyl-5,6-dihydropyrazolo-[5,1-a]isoquinolin-5-one | 20 parts |
|---|---|
| Sodium ligninsulfonate | 2 parts |
| Polyoxyethylene alkyl ether | 2 parts |

The above ingredients were mixed to give a wettable powder.

EXAMPLE 28

(Plant growth regulating composition):

| 2-(4-Fluorophenyl)-5,6-dihydro-pyrazolo[5,1-a]isoquinolin-5-one | 10 parts |
|---|---|
| Tween 20 (trademark) | 1 part |
| Ethanol | 89 parts |

The above ingredients were mixed to give a solution.

EXAMPLE 29

(Plant growth regulating composition):

| 2-(4-Fluorophenyl)-5,6-dihydro-pyrazolo[5,1-a]isoquinolin-5-one | 10 parts |
|---|---|
| Xylene | 40 parts |
| Dimethylformamide | 30 parts |
| Sorpol 9048 (trademark) | 20 parts |

The above ingredients were mixed to give an emulsifiable concentrate.

EXAMPLE 30

(Plant growth regulating composition):

| | |
|---|---|
| 2-(4-Fluorophenyl)-5,6-dihydro-pyrazolo[5,1-a]isoquinolin-5-one | 1 part |
| Xylene | 4.5 parts |
| Dimethylsulfoxide | 10 parts |
| Sorpol 2680H (trademark) | 4.5 parts |

The above ingredients were mixed to give an emulsifiable concentrate.

We claim:

1. A pyrazoloisoquinoline derivative of the general formula:

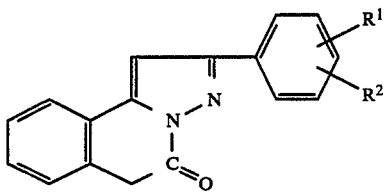

wherein $R^1$ and $R^2$ are the same or different and each is a hydrogen or halogen atom or a nitro, lower alkyl, halogen-substituted alkyl, lower alkoxy, lower alkylthio or aryloxy selected from the group consisting of phenoxy, tolyloxy, xylyloxy, mesityloxy and naphthoxy.

2. A compound of claim 1, wherein $R^1$ is a halogen atom and $R^2$ is a hydrogen atom.

3. A compound of claim 2, wherein $R^1$ is a fluorine atom.

4. A compound of claim 3, wherein $R^1$ is 4-fluoro.

5. A plant growth regulating composition which comprises, as active ingredients, an effective regulating amount of one or more pyrazoloisoquinoline derivatives of the general formula:

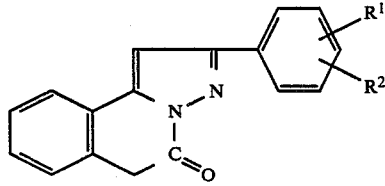

wherein $R^1$ and $R^2$ are the same or different and each is a hydrogen or halogen atom or a nitro, lower alkyl, halogen-substituted alkyl, lower alkoxy, lower alkylthio or aryloxy selected from the group consisting of phenoxy, tolyloxy, xylyloxy, mesityloxy and naphthoxy.

6. A plant growth regulating composition comprising:

(a) an effective regulating amount of a pyrazoloisoquinoline derivative of the general formula:

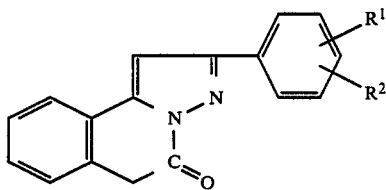

wherein $R^1$ and $R^2$ are the same or different and each is a hydrogen or halogen atom or a nitro, lower alkyl, halogen-substituted alkyl, lower alkoxy, lower alkylthio or aryloxy selected from the group consisting of phenoxy, tolyloxy, xylyloxy, mesityloxy and naphthoxy, and (b) an agrochemically acceptable carrier.

7. A method for regulating the growth of plants comprising spraying onto said plants an effective regulating amount of the plant growth regulating composition of claims 5 or 6.

8. A method for increasing the yield of cereal crops comprising spraying onto said cereal an effective amount of crops the plant growth regulating composition of claims 5 or 6.

9. A method for increasing the yield of leguminous crops comprising spraying onto said leguminous plants an effective amount of the plant growth regulating composition of claims 5 or 6.

10. A method for increasing the yield of a potato crop comprising spraying onto said potato crop an effect amount of the plant growth regulating composition of claims 5 or 6.

11. A method for controlling the plant height of grasses (mono-cotyledon) comprising spraying onto said grasses an effective amount of the plant growth regulating composition of claims 5 or 6.

12. A method for controlling the abscission formation of flowers, fruits or leaves of plants comprising spraying onto said plants an effective amount of the plant growth regulating composition of claims 5 or 6.

13. A plant growth regulating composition of claims 5 or 6, wherein the active ingredient is a compound wherein $R^1$ is a halogen atom and $R^2$ is a hydrogen atom.

14. A plant growth regulating composition of claims 5 or 6, wherein the active ingredient is a compound wherein $R^1$ is a fluorine atom and $R^2$ is a hydrogen atom.

15. A plant growth regulating composition of claims 5 or 6 wherein the active ingredient is a compound wherein $R^1$ is 4-fluoro and $R^2$ is a hydrogen atom.

16. A method of claims 7, 8, 9, 10, 11 or 12, wherein the active ingredient of the plant growth regulating composition is a compound wherein $R^1$ is a halogen atom and $R^2$ is a hydrogen atom.

17. A method of claims 7, 8, 9, 10, 11 or 12, wherein the active ingredient of the plant growth regulating composition is a compound wherein $R^1$ is a fluorine atom and $R^2$ is a hydrogen atom.

18. A method of claims 7, 8, 9, 10, 11 or 12, wherein the active ingredient of the plant growth regulating composition is a compound wherein $R^1$ is 4-fluoro and $R^2$ is a hydrogen atom.

* * * * *